(12) United States Patent
Alarcon

(10) Patent No.: US 9,574,057 B2
(45) Date of Patent: Feb. 21, 2017

(54) HYDROGEL ADHESION TO MOLDED POLYMERS

(71) Applicant: Becton, Dickinson and Company, Franklin Lakes, NJ (US)

(72) Inventor: Javier Alarcon, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 116 days.

(21) Appl. No.: 14/388,886

(22) PCT Filed: Mar. 28, 2013

(86) PCT No.: PCT/US2013/034290
§ 371 (c)(1),
(2) Date: Sep. 29, 2014

(87) PCT Pub. No.: WO2013/148957
PCT Pub. Date: Oct. 3, 2013

(65) Prior Publication Data
US 2015/0025170 A1   Jan. 22, 2015

Related U.S. Application Data

(60) Provisional application No. 61/616,735, filed on Mar. 28, 2012.

(51) Int. Cl.
| | | |
|---|---|---|
| C08F 2/46 | (2006.01) | |
| C08F 2/50 | (2006.01) | |
| C08G 61/04 | (2006.01) | |
| C08J 7/18 | (2006.01) | |
| A61B 5/145 | (2006.01) | |
| A61B 5/1455 | (2006.01) | |
| G01N 33/66 | (2006.01) | |
| C07K 17/04 | (2006.01) | |

(52) U.S. Cl.
CPC .............. *C08J 7/18* (2013.01); *A61B 5/14532* (2013.01); *A61B 5/14556* (2013.01); *C07K 17/04* (2013.01); *G01N 33/66* (2013.01); *A61B 2562/028* (2013.01); *C08J 2323/12* (2013.01); *C08J 2325/06* (2013.01); *C08J 2367/03* (2013.01); *C08J 2369/00* (2013.01)

(58) Field of Classification Search
CPC ....... C08J 7/18; C08J 2323/12; C08J 2369/00; C08J 2325/06; C08J 2367/03; G01N 33/66; A61B 5/14532; A61B 2562/028; A61B 5/14556; C07K 17/04
USPC ........... 522/40, 33, 6, 71, 189, 184, 1; 520/1
See application file for complete search history.

(56) References Cited

U.S. PATENT DOCUMENTS

| | | | |
|---|---|---|---|
| 4,636,534 A | 1/1987 | Nawata et al. | |
| 6,214,049 B1 | 4/2001 | Gayer et al. | |
| 6,458,468 B1* | 10/2002 | Moskala | ............ C08J 7/047 |
| | | | 428/413 |
| 2002/0155425 A1 | 10/2002 | Han et al. | |
| 2005/0239155 A1 | 10/2005 | Alarcon et al. | |
| 2007/0138667 A1* | 6/2007 | Dang | ........... B29C 37/0032 |
| | | | 264/1.32 |
| 2007/0154395 A1* | 7/2007 | Morris | ............ G01N 33/66 |
| | | | 424/9.6 |
| 2007/0225823 A1* | 9/2007 | Hawkins | ............ A61L 27/28 |
| | | | 623/23.51 |
| 2008/0003663 A1 | 1/2008 | Bryhan et al. | |
| 2010/0032090 A1* | 2/2010 | Myung | ............ A61K 6/09 |
| | | | 156/275.5 |
| 2010/0304399 A1 | 12/2010 | Lee et al. | |
| 2011/0015364 A1 | 1/2011 | Hibino et al. | |
| 2011/0112250 A1 | 5/2011 | Esseghir et al. | |

FOREIGN PATENT DOCUMENTS

| | | |
|---|---|---|
| WO | WO 00/44819 A1 | 8/2000 |
| WO | WO 2004/046726 A2 | 6/2004 |
| WO | WO 2007/087402 A2 | 8/2007 |
| WO | WO 2007/097922 A2 | 8/2007 |
| WO | WO 2008/131360 A1 | 10/2008 |
| WO | WO 2008/142158 A2 | 11/2008 |

OTHER PUBLICATIONS

PCT International Search Report and Written Opinion for PCT/US2013/034290 dated Jun. 5, 2013.
Supplemental European Search Report dated Mar. 21, 2016 that issued in a counterpart Patent Application No. 13767389.3.
Supplemental Partial European Search Report dated Oct. 16, 2015 that issued in a counterpart Patent Application No. 13767389.3.
European Office Action dated Nov. 11, 2016 which issued in a counterpart Patent Application No. 13767389.3.

* cited by examiner

*Primary Examiner* — Ling Choi
*Assistant Examiner* — Jessica E Whiteley
(74) *Attorney, Agent, or Firm* — Dickinson Wright PLLC

(57) ABSTRACT

Methods for adhering a hydrogel matrix to a molded polymer substrate and its use as a biosensor, e.g., a continuous or episodic glucose monitor, are disclosed. The presently disclosed subject matter provides a method for adhering a hydrogel matrix to a molded polymer substrate, the method comprising: (a) molding a polymer comprising one or more polymer chains with an oxidizer to form a molded polymer substrate; (b) providing a hydrogel matrix comprising a hydrogel, a component comprising one or more acrylate groups or another functional group that can form one or more radicals upon polymerization in the molded polymer substrate, and a photo initiator; (c) combining the molded polymer substrate and the hydrogel matrix; and (d) curing the combined molded polymer substrate and hydrogel matrix for a period of time.

15 Claims, 2 Drawing Sheets

HYDROGEL ADHESION TO MOLDED POLYMERS

REFERENCE TO RELATED APPLICATIONS

This application is a 35 U.S.C. §371 U.S. national phase entry of International Application No. PCT/US2013/034290 having an international filing date of Mar. 28, 2013, which claims the benefit of U.S. Provisional Application No. 61/616,735, filed on Mar. 28, 2012, which is hereby incorporated by reference for all purposes as if fully set forth herein.

BACKGROUND

In the past, physical entrapment typically was used to immobilize detection matrices on a molded polymer substrate in analytical systems designed for the diagnostic testing of liquid samples, e.g., biological samples from a patient or subject. In such systems, the molded substrate physically holds the detection matrix in place. Analytical testing, however, is not feasible in such systems, especially with dense or colored liquids, because the detection matrix has a tendency to slide or move away from its original position on the substrate. Under these circumstances, the liquid sample can infiltrate between the substrate and the detection matrix and potentially interfere with optical measurements. Further, in optical measurements, the matrix can move out of the focal point of the interrogating light source, causing inaccurate or even false negative readings.

SUMMARY

In some aspects, the presently disclosed subject matter provides a method for adhering a hydrogel matrix to a molded polymer substrate, the method comprising: (a) molding a polymer comprising one or more polymer chains with an oxidizer to form a molded polymer substrate, wherein the oxidizer breaks the one or more polymer chains, and wherein the one or more polymer chains can recombine while retaining one or more putative radicals in the molded polymer substrate; (b) providing a hydrogel matrix comprising a hydrogel, a component comprising one or more acrylate groups or another functional group that can form one or more radicals upon polymerization in the molded polymer substrate, and a photoinitiator; (c) combining the molded polymer substrate and the hydrogel matrix; and (d) curing the combined molded polymer substrate and hydrogel matrix for a period of time to covalently bind the hydrogel matrix to the molded polymer substrate, thereby adhering the hydrogel matrix to the molded polymer substrate.

In some aspects, the hydrogel matrix further comprises a protein-reporter group, which in some aspects comprises a glucose binding protein (GBP). In certain aspects, the reporter group comprises a fluorescent dye.

In further aspects, the presently disclosed subject matter provides a biosensor comprising a hydrogel matrix covalently bound to a molded polymer substrate, wherein the hydrogel matrix further comprises a protein-reporter group. In certain aspects, the protein comprises a glucose binding protein (GBP) and the reporter group comprises a fluorescent dye. In particular aspects, the biosensor is a glucose sensor that is used to determine the presence or amount of glucose in a biological sample.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
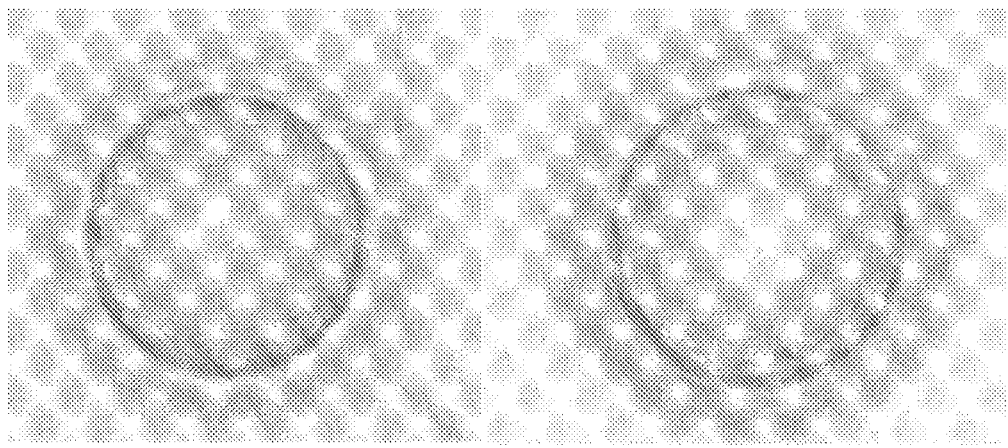
Figure 2:
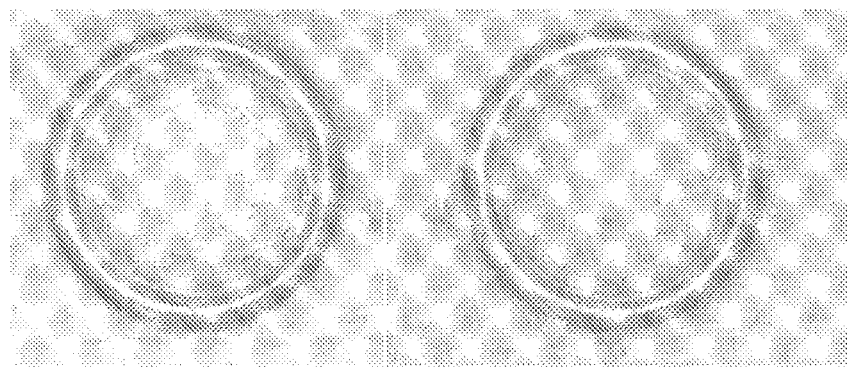

Having thus described the presently disclosed subject matter in general terms, reference will now be made to the accompanying Figures, which are not necessarily drawn to scale, and wherein:

FIG. 1 shows (left panel) a representative substrate (polycarbonate) and (right panel) matrix after dry process; and FIG. 2 shows (left panel) a representative substrate (polystyrene) and (right panel) matrix after dry process.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Hydrogel Adhesion to a Molded Polymer Substrate

The presently disclosed subject matter provides methods for adhering a detection matrix, e.g., a hydrogel matrix, to a moldable polymer substrate. In methods known in the art, physical entrapment is used to immobilize the detection matrix onto the polymer substrate. In such systems, the molded substrate physically holds the detection matrix in place. The detection matrix, however, has a tendency to slide or move away from its original position on the substrate in such systems. Under these circumstances, analytical testing is not feasible, especially in dense or colored liquids. In such cases, the liquid under test can infiltrate between the substrate and the matrix, potentially interfering with optical measurements.

Generally, the presently disclosed methods for adhering a hydrogel matrix to a molded substrate include two stages. The first stage includes molding a polymer mix with an oxidizer to form a molded polymer substrate. The oxidizer breaks the polymer chains, which can recombine while retaining some putative radicals in the molded part. The second stage includes polymerizing hydrogels with acrylate groups or other materials that can form radicals upon polymerization in the molded substrate.

When the material prepared in the first stage, i.e., the molded polymer substrate, is combined with the material prepared in the second stage, i.e., the polymerized hydrogel, and cured, e.g., under ultraviolet (UV) light or heat, the hydrogel binds covalently to the molded polymer substrate, thereby promoting adhesion of the hydrogel to the substrate.

Accordingly, the final product, i.e., a molded substrate having a hydrogel matrix covalently bound thereto, can undergo various chemical and physical processes without the bound hydrogel moving away from its original position on the substrate. Thus, the presently disclosed methods and materials facilitate the development of new processes and combinations of materials.

Another feature of the presently disclosed system is that other methods of binding materials to a plastic substrate, such as with plasma treatment, are not as efficient. As provided herein below, hydrogels provide binding to the substrate with plasma treatment, but with time, the hydrogel often separates from the substrate. In contrast, the presently disclosed subject matter provides a covalent attachment of the hydrogel matrix to the substrate. Such features make the presently disclosed methods and materials attractive for storage stability.

Accordingly, in some embodiments, the presently disclosed subject matter provides a method for adhering a hydrogel matrix to a molded polymer substrate, the method comprising: (a) molding a polymer comprising one or more polymer chains with an oxidizer to form a molded polymer substrate, wherein the oxidizer breaks the one or more polymer chains, and wherein the one or more polymer chains can recombine while retaining one or more putative radicals in the molded polymer substrate; (b) providing a hydrogel matrix comprising a hydrogel, a component comprising one or more acrylate groups or another functional group that can form one or more radicals upon polymerization in the molded polymer substrate, and a photoinitiator; (c) combining the molded polymer substrate and the hydrogel matrix; and (d) curing the combined molded polymer substrate and hydrogel matrix for a period of time to covalently bind the hydrogel matrix to the molded polymer substrate, thereby adhering the hydrogel matrix to the molded polymer substrate.

Generally, a "hydrogel" is a three-dimensional network of crosslinked hydrophilic polymers that are typically insoluble or poorly soluble in water, but can swell to an equilibrium size when dispersed in excess water. Hydrogel compositions can include, without limitation, for example, poly(ethylene glycol), poly(ethylene oxide), poly(vinyl alcohol), polyvinylpyrrolidone, polyacrylates, such as poly(hydroxyethyl methacrylate), poly(esters), poly(hydroxy acids), poly(lactones), poly(amides), such as poly(acrylamide), poly(esteramides), poly(amino acids), poly(anhydrides), poly(orthoesters), poly(carbonates), poly(phosphazines), poly(thioesters), polysaccharides, sol gels and or polymers generated out of siloxanes, and tetraalkylammonium, or other polymers or copolymers having an abundance of hydrophilic groups, and mixtures thereof.

Hydrogels also can include, for example, a poly(hydroxy) acid, including poly(alpha-hydroxy) acids and poly(beta-hydroxy) acids. Such poly(hydroxy) acids include, for example, polylactic acid, polyglycolic acid, polycaproic acid, polybutyric acid, polyvaleric acid, and copolymers and mixtures thereof. One of ordinary skill in the art would recognize that the constituents making up the hydrogel can be modified to change the hydrophobicity and charge of the hydrogel if so desired.

Moldable polymers suitable for use with the presently disclosed methods include, but are not limited to, polycarbonates, polystyrenes, polyethylenes, copolyesters, such as polyethylene terephthalate (PET), and polypropylenes.

The oxidizer can be a peroxide, including, but not limited to t-butyl phenyl peroxide, lauroyl peroxide, and dicumyl peroxide. In particular embodiments, the peroxide is t-butyl phenyl peroxide. The raw polymer can be mixed with a weight percent of peroxide ranging from about 0.1% to about 0.4%. In particular embodiments, the weight percent of peroxide is about 0.2%.

In some embodiments, the photoinitiator is selected from the group consisting of 2-hydroxy-2-methylpropiophenone, 2,2-dimethyl-2-phenylacetophenone, p-(octyloxyphenyl) phenyliodonium hexafluoroantimonate, bis-acyl-phosphine oxide (BAPO) in water, and a liquid mixture of an oligomeric α-hydroxyketone (oligomeric 2-hydroxy-2-methyl-1, 4-(1-methylvinyl)-phenylpropanone) and 2-hydroxy-2-methyl-1-phenyl-1-propanone. In particular embodiments, the photoinitiator is 2-hydroxy-2-methylpropiophenone.

The presently disclosed methods provide for analytical or diagnostic testing on such hydrogels bound to a moldable polymer substrate, e.g., a plastic. The materials prepared by the presently disclosed methods can be incorporated into well plates, individual laminate sensors, or any other format suitable for episodic or continuous testing. Further, because the hydrogel can bind an interrogating analyte, an analytical sensor can be made from this platform. Such sensors can be tested with water, buffers, or any biological fluids.

The presently disclosed biosensors can be used in combination with binding protein assays to detect physiologically important molecules, including metabolites, such as glucose, fatty acids, and lactates, in biological samples.

Of particular interest is testing of viscous and/or non-transparent samples, because the test article can be poured on top of the hydrogel and it will not interfere with the analytical interrogation of the analyte. Systems known in the art only allow for the use of clear liquids that did not interfere with the optical path of the sensing unit. With the matrix bound firmly to the molded substrate, the presently disclosed methods and materials allow the use of any kind of dense or colored liquid without interference with optical measurements.

In some embodiments, the hydrogel can incorporate a protein-reporter group, e.g., a glucose binding protein labeled with a fluorescent dye, which can function as a biosensor. In such embodiments, the binding domains of the protein-reporter group are either physically entrapped in and surrounded by the hydrogel or the domains are covalently bound to and surrounded by the hydrogel. One of ordinary skill in the art would recognize that any protein can be included in the hydrogel matrix. In representative embodiments, the protein can be a horseradish peroxidase or an antibody.

In particular embodiments, the protein comprises a glucose binding protein (GBP). In some embodiments, the GBP is from *E. coli*. Such GBPs also are referred to as a D-galactose/D-glucose binding protein (GGBP). One of ordinary skill in the art would recognize that various GBPs can be used in the presently disclosed methods. For example, thermophilic GBPs, such as tmGBP from *Thermotoga maritime*, are even more stable at higher temperatures than the *E. coli* GBP using the methods of the presently disclosed subject matter.

More particularly, the term "glucose/galactose binding protein" or "GGBP" as used herein refers to a type of protein naturally found in the periplasmic compartment of bacteria. These periplasmic proteins are naturally involved in chemotaxis and transport of small molecules (e.g., sugars, amino acids, and small peptides) into the cytoplasm. For example, GGBP is a single chain protein consisting of two globular domains that are connected by three strands to form a hinge. The binding site is located in the cleft between the two domains. When glucose enters the binding site, GGBP undergoes a conformational change, centered at the hinge, which brings the two domains together and entraps glucose in the binding site. The wild type *E. coli* GGBP DNA and amino acid sequence can be found at www.ncbi.nlm.nih.gov/entrez/accession number D90885 (genomic clone) and accession number 23052 (amino acid sequence).

As used herein, a "derivative of a protein" is a protein that shares substantial sequence identity with the wild-type protein. Derivative proteins of the presently disclosed subject matter can be made or prepared by techniques well known to those of skill in the art. Examples of such techniques include, but are not limited to, mutagenesis and direct synthesis. Derivative proteins also can be modified, either by natural processes, such as post-translational processing, or by chemical modification techniques which are well known in the art. Such modifications are well described in basic texts and in more detailed monographs, as well as in voluminous research literature. Modifications can occur anywhere in the polypeptide chain, including the peptide backbone, the amino acid side-chains and the amino or carboxyl termini. It will be appreciated that the same type of modification can be present in the same or varying degrees at several sites in a given polypeptide or protein. Also, a given polypeptide or protein can contain more than one modification. Examples of modifications include, but are not limited to, glycosylation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Polypeptides or proteins can even be branched as a result of ubiquitination, and they can be cyclic, with or without branching. (See, e.g., T E. Creighton, Proteins—Structure And Molecular Properties, 2nd ed., W.H. Freeman and Company, New York (1993); Wold, F., "Posttranslational Protein Modifications: Perspectives and Prospects," in Posttranslational Covalent Modification Of Proteins, B. C. Johnson, Ed., Academic Press, New York (1983); Seifter et al., Methods in Enzymol, 182:626-646 (1990) and Rattan et al., Ann NY Acad Sci., 663:48-62 (1992), each of which is incorporated herein by reference. Examples of derivative proteins include, but are not limited to, mutant and fusion proteins.

A "mutant protein" is used herein as it is known in the art. In general, a mutant protein can be created by addition, deletion or substitution of the wild-type primary structure of the protein or polypeptide. Mutations include, for example, the addition or substitution of cysteine groups, non-naturally occurring amino acids, and replacement of substantially non-reactive amino acids with reactive amino acids. A mutant protein can be mutated to bind more than one analyte in a specific manner. Indeed, the mutant proteins can possess specificity towards its wild-type analyte and another target ligand. Likewise, a mutant protein can be able to only bind an analyte or analytes that the wild-type binding protein does not bind. Methods of generating mutant proteins are well-known in the art. For example, Looger, L. L. et al., Nature 423 (6936): 185-190 (2003), which is incorporated herein by reference, disclose methods for redesigning binding sites within periplasmic binding proteins that provide new analyte-binding properties for the proteins. These mutant binding proteins retain the ability to undergo conformational change, which can produce a directly generated signal upon analyte-binding. By introducing between 5 and 17 amino acid changes, Looger, et al. constructed several mutant proteins, each with new selectivities for TNT (trinitrotoluene), L-lactate, or serotonin. For example, Looger et al. generated L-lactate binding proteins from GGBP. Other mutations to GGBP are found in Looger L. L. et al., Nature 423: 185-190, (2003), which is incorporated herein by reference in its entirety.

Examples of mutations of a GGBP protein, for example the GGBP protein of GenBank Accession No. PO2927 without the 23 amino acid leader sequence (i.e., the mature chain), include, but are not limited to, having a cysteine substituted for lysine at position 11 (K11C), a cysteine substituted for aspartic acid at position 14 (D14C), a cysteine substituted for valine at position 19 (V19C), a cysteine substituted for asparagine at position 43 (N43C), a cysteine substituted for glycine at position 74 (G74C), a cysteine substituted for tyrosine at position 107 (Y107C), a cysteine substituted for threonine at position 110 (T110C), a cysteine substituted for serine at position 112 (S112C), a double mutant including a cysteine substituted for serine at position 112 and serine substituted for leucine at position 238 (S112C/L238S), a cysteine substituted for lysine at position 113 (K113C), a cysteine substituted for lysine at position 137 (K137C), a cysteine substituted for glutamic acid at position 149 (E149C), a double mutant including a cysteine substituted for glutamic acid at position 149 and an arginine substituted for alanine at position 213 (E149C/A213R), a double mutant including a cysteine substituted for glutamic acid at position 149 and a serine substituted for leucine at position 238 (E149C/L238S), a double mutant including a serine substituted for alanine at position 213 and a cysteine substituted for histidine at position 152 (H152C/A213S), a cysteine substituted for methionine at position 182 (M182C), a cysteine substituted for tryptophan at position 183 (W183C), a cysteine substituted for alanine at position 213 (A213C), a double mutant including a cysteine substituted for alanine at position 213 and a cysteine substituted for leucine at position 238 (A213C/L238C), a cysteine substituted for methionine at position 216 (M216C), a cysteine substituted for aspartic acid at position 236 (D236C), a cysteine substituted for leucine at position 238 (L238C) a cysteine substituted for aspartic acid at position 287 (D287C), a cysteine substituted for arginine at position 292 (R292C), a cysteine substituted for valine at position 296 (V296C), a triple mutant including a cysteine substituted for glutamic acid at position 149 and a serine substituted for alanine at position 213 and a serine substituted for leucine at position 238 (E149C/A213S/L238S), a triple mutant including a cysteine substituted for glutamic acid at position 149 and an arginine substituted for alanine at position 213 and a serine substituted for leucine at position 238 (E149C/A213R/L238S), a cysteine substituted for glutamic acid at position 149 and a cysteine substituted for alanine at position 213 and a serine substituted for leucine at position 238 (E149C/A213C/L238S). Another example includes a mutated GGBP having the following substitutions: N391, G82E, Q83K, N84D, Q175E, Q177H, L178M, W183C, N259E and N260S (referred to as "SM4"). Additional embodiments include mutations of GGBP at Y10C, N15C, Q26C, E93C, H152C, M182C, W183C, L255C, D257C, P294C, and V296C. Other mutated GGBPs are disclosed in U.S. Patent Publication No. 2008-0044856, which is incorporated herein by reference in its entirety.

The mutation can serve one or more of several purposes. For example, a naturally occurring protein can be mutated to change the long-term stability, including thermal stability, of the protein, to conjugate the protein to a particular encapsulation matrix or polymer, to provide binding sites for detectable reporter groups, to adjust its binding constant with respect to a particular analyte, or combinations thereof.

The analyte and mutated protein can act as binding partners. The term "associates" or "binds" as used herein refers to binding partners having a relative binding constant (Kd) sufficiently strong to allow detection of binding to the protein by a detection means. The Kd can be calculated as the concentration of free analyte at which half the protein is bound, or vice versa. When the analyte of interest is glucose, the Kd values for the binding partners are between about 0.0001 mM and about 50 mM. Mutations of binding proteins are described in U.S. Pat. No. 7,064,103 to Pitner et al., issued Jun. 20, 2006, U.S. Pat. No. 6,855,556 to Amiss et al., issued Feb. 15, 2005, and U.S. Patent Application Publication No. 2006/0280652, filed May 18, 2005, each of which is incorporated by reference in its entirety.

In addition to changing binding characteristics, derivative proteins also can be used to incorporate a fluorophore, e.g., a fluorescent dye, onto or within the binding member.

As used herein, the term "fluorophore" is meant to include a moiety of a larger molecule or conjugate that can be induced to emit fluorescence when irradiated, i.e., excited, by electromagnetic radiation of an appropriate wavelength. More particularly, a fluorophore can be a functional group of a molecule or conjugate that absorbs light of a certain wavelength and emits light at different wavelength. The intensity and the wavelength of the light emitted, as well as other fluorescence properties including, but not limited to, fluorescence lifetime, anisotropy, polarization, and combinations thereof, depend on the identity of the fluorophore and its chemical environment. A fluorophore can include a fluorescent molecule, such as the presently disclosed fluorescent dyes.

Representative fluorophores suitable for use with the presently disclosed subject matter include those disclosed in U.S. Patent Application Publication No. 2011/0184168, for Long Wavelength Thiol-Reactive Fluorophores, to J. B. Pitner, et al., published Jul. 28, 2011; U.S. Patent Application Publication No. 2010/0167417, for Long Wavelength Thiol-Reactive Fluorophores, to J. B. Pitner, et al., published Jul. 1, 2010; U.S. Patent Application Publication No. 2010/0003763, for Long Wavelength Thiol-Reactive Fluorophores, to J. B. Pitner, et al., published Jan. 7, 2010; U.S. Patent Application Publication No. 2008/0311675, for Dyes Having Ratiometric Fluorescence Response for Detecting Metabolites, to J. Thomas, et al., published Dec. 18, 2008; U.S. Patent Application Publication No. 2006/0280652, for Long Wavelength Thiol-Reactive Fluorophores, to J. B. Pitner, et al., published Dec. 14, 2006; U.S. Pat. No. 8,129,525, for Long Wavelength Thiol-Reactive Fluorophores, to J. B. Pitner, et al., issued Mar. 6, 2012; U.S. Pat. No. 8,071,794, for Long Wavelength Thiol-Reactive Fluorophores, to J. B. Pitner, et al., issued Dec. 6, 2011; U.S. Pat. No. 7,767,821, for Long Wavelength Thiol-Reactive Fluorophores, to J. B. Pitner, et al., issued Aug. 3, 2010; and U.S. Pat. No. 7,563,891, for Long Wavelength Thiol-Reactive Fluorophores, to J. B. Pitner, et al., issued Jul. 21, 2009, each of which is incorporated herein by reference in its entirety.

The fluorophores can be used to indicate a change in the binding member, including, but not limited to, three-dimensional conformational changes, changes in orientation of the amino acid side chains of proteinaceous binding domains, and redox states of the binding member. With the addition/substitution of one or more residues into the primary structure of a protein, some of the labeling moieties used in the current methods and compositions can be attached through chemical means, such as reduction, oxidation, conjugation, and condensation reactions. Examples of residues commonly used to label proteins include, but not are limited to, lysine and cysteine. For example, any thiol-reactive group can be used to attach a fluorophore to a naturally occurring or engineered cysteine in the primary structure of the polypeptide. Also, for example, lysine residues can be labeled using succinimide ester derivatives of fluorophores. See Richieri, G. V. et al., J. Biol. Chem., 267: 23495-501 (1992), which is incorporated herein by reference. The fluorophore can be attached at a site on the binding protein so that the conformational change maximizes the change in fluorescence properties.

The fluorophore can be attached to the mutated protein, for example a GGBP, by any conventional means known in the art. For example, the reporter group can be attached via amines or carboxyl residues on the protein. Other embodiments include covalent coupling via thiol groups on cysteine residues of the mutated or native protein. For example, for mutated GGBP, cysteines can be located at position 10, at position 11, position 14, at position 15, position 19, at position 26, at position 43, at position 74, at position 92, at position 93, position 107, position 110, position 112, at position 113, at position 137, at position 149, at position 152, at position 154, at position 182, at position 183, at position 186, at position 211, at position 213, at position 216, at position 238, at position 240, at position 242, at position 255, at position 257, at position 287, at position 292, at position 294, and at position 296.

As used herein, the term "binding protein" or "binding member" refers to a protein, that when conjugated with a fluorophore, interacts with a specific analyte or ligand in a manner capable of producing a detectable florescence signal differentiable from when a target analyte or ligand is present or absent, or when a target analyte or ligand is present in varying concentrations over time. The term "producing a detectable signal" refers to the ability to recognize a change in a property of a reporter group, e.g., a fluorophore, in a manner that enables the detection of ligand-protein binding. Further, the producing of a detectable signal can be reversible or non-reversible. The signal-producing event includes continuous, programmed, and episodic means, including one-time or reusable applications. The reversible signal-producing event can be instantaneous or can be time-dependent, so long as a correlation with the presence or concentration of analyte is established.

The binding member may be at least one fragment of a receptor. As used herein, the term "receptor" refers to a protein macromolecule having an active site capable of binding a ligand. More particularly, a "receptor" refers to an antibody, a hormone or bacterial receptor, an affinity protein, a transport protein, a viral receptor, or any polypeptide having a specific affinity for a ligand.

As used herein, the term "ligand" refers to any molecule capable of binding to the receptor via an active site. For example, the ligand may be a protein, a peptide or hapten antigen, such as a bacterial antigen, or a hormone, a cytokine, an interleukin, a tumor necrosis factor (TNF) a growth factor, a viral protein, or a peptide or nucleotide sequence.

As used herein, the term "active site" when referring to, for example, "an active site of the receptor or of the receptor fragment" refers to amino acid residues of the receptor or receptor fragment that contribute to the binding of the ligand. This active site also can be referred to as a "binding site" or "paratope."

The term "proximity" as used herein refers to the position of amino acid residues of the receptor that are in direct contact with the ligand, those that are in contact by water molecules, and those for which the solvent accessible surface area (ASA), as that term in known in the art, see, e.g., Creighton, T. E., "Proteins: Structure and molecular properties," 2nd ed., (W.H. Freeman & Co., New York) 227-229 (1993), is modified by the binding of the ligand.

The change in the detectable characteristics of GBP can be used in a biosensor. As used herein, the term "biosensor" and "biosensor compound" refers to a compound that undergoes a detectable change in specific response to a ligand or target analyte. Without wishing to be bound to any one particular theory, the binding protein comprising the biosensor can adopt two conformations: a ligand-free open form and a closed form when bound to a ligand. These two conformations can interconvert, for example, via a global hinge-binding mechanism upon ligand binding or changes in ligand concentration. By positioning environmentally-sensitive dyes in locations that undergo local conformational changes in concert with these global conformational changes, such ligand-mediated conformational changes can be exploited to couple ligand binding to a color change. Accordingly, these engineered conformational coupling mechanisms enable reagentless optical biosensors to be formed from selected binding proteins and environmentally-sensitive dyes.

Fluorescent dyes in biosensors exhibit a change in intensity of the fluorescence signal, a shift in the emission wavelength of the maximum fluorescence emission, a change in fluorescence lifetime, a change in anisotropy, a change in polarization, or a combination thereof, when the binding protein undergoes a conformational change as a result of changes in the glucose concentration. An energy source, such as a laser or LED, is applied to the biosensor to excite the fluorescent dye, and a fluorescence property is detected. Due to either a conformational change in the binding protein, subsequent changes in the microenvironment of the dye, or both, the detected fluorescence property or change of the detected fluorescence property can be correlated to the presence of an analyte or a analyte concentration. The fluorescence and detection can be carried out continuously or intermittently at predetermined times. Thus, a biosensor can have episodic or continuous sensing of analyte, for example, glucose.

The fluorescent dye can be covalently attached to the binding protein in a site-specific manner to obtain the desired change in the fluorescence. The fluorescent dye is attached at a site on the binding protein so that the conformational change maximizes the change in fluorescence properties. In other embodiments, the fluorescent dyes may have a thiol-reactive group that can be coupled to the thiol group on a cysteine residue of the binding protein. Fluorescent dyes include, but are not limited to, derivatives of the squaraine nuclei, benzodioxazole nuclei, Nile Red nuclei, coumarin nuclei and aza coumarin nuclei. Fluorophores that operate at long emission wavelengths (for example, about 575 nm or greater) are used when the molecular sensor is to be used in vivo, for example, incorporated into an implantable biosensor device (the skin being opaque below about 575 nm).

To accurately determine glucose concentration in biological solutions, such as blood, interstitial fluids, occular solutions or perspiration, and the like, it may be desirable to adjust the binding constant of the sensing molecule of a biosensor so as to match the physiological and/or pathological operating range of the biological solution of interest. Without the appropriate binding constant, a signal may be out of range for a particular physiological and/or pathological concentration. Additionally, biosensors may be configured using more than one protein, each with a different binding constant, to provide accurate measurements over a wide range of glucose concentrations as disclosed by Lakowicz (U.S. Pat. No. 6,197,534).

Embodiments that exhibit a shift in emission wavelength upon ligand binding enable a biosensor comprising a fluorophore to be self-referencing. In such embodiments, the fluorophore exhibits an increase in a first emission wavelength in the presence of a metabolite, such as glucose, and a decrease in a second emission wavelength. A ratio between the first emission wavelength and the second wavelength can be calculated to determine the concentration of glucose in the sample under test. Such self referencing can correct for variations in excitation source intensity and other sources of noise and instability in the biosensor without requiring a reference dye. Thus, a single excitation wavelength can be used to observe a ratiometric response in the fluorescence output of the biosensor. As used herein, the term "ratiometric response" means that the intensities of the first emission wavelength and the second emission wavelength vary independently such that the ratio of the two emission wavelengths (the "ratiometric quotient" or "QR") can be used to indicate the presence and/or amount, e.g., concentration, of the ligand or analyte in a sample. See U.S. Patent Application Publication No. 2009/0104714, for Visual Glucose Sensor and Methods of Use Thereof, to J. Thomas, et al., published Apr. 23, 2009, which is incorporated herein by reference in its entirety. Thus, in some embodiments, the biosensor is a glucose sensor that is used to determine the presence or amount of glucose in a biological sample. A glucose sensor can be used in vitro or in vivo to follow the kinetics of biological reactions involving glucose, as well as to monitor the amount of glucose in a sample. The glucose sensors of the presently disclosed subject matter are capable of measuring or detecting micromolar to molar glucose concentrations without reagent consumption.

As used herein, the term "biological sample" includes any liquid or fluid sample, including a sample derived from a biological source, such as a physiological fluid, including whole blood or whole blood components, such as red blood cells, white blood cells, platelets, serum and plasma; ascites; urine; saliva; sweat; milk; synovial fluid; peritoneal fluid; amniotic fluid; percerebrospinal fluid; lymph fluid; lung embolism; cerebrospinal fluid; pericardial fluid; cervicovaginal samples; tissue extracts; cell extracts; and other constituents of the body that are suspected of containing the analyte of interest. In addition to physiological fluids, other liquid samples, such as water, food products and the like, for the performance of environmental or food production assays are suitable for use with the presently disclosed subject matter. A solid material suspected of containing the analyte also can be used as the test sample. In some instances it might be beneficial to modify a solid test sample to form a liquid medium or to release the analyte.

The presently disclosed biosensor devices are suitable for use in various settings, including in vivo, in vitro and in situ. Such devices include medical devices or implants for monitoring metabolic substrate levels in a subject. When such devices are implanted in a subject, the implants should be biocompatible such that they produce little or no detectable inflammation/rejection reaction. One approach for rendering the implants more biocompatible comprises coating the implants with biocompatible polymers, such as poly(urethane) elastomers, poly(urea) and poly(vinylchloride). Exemplary biosensor devices are described in U.S. Patent Application Publication No. 2006/0078908, filed Jun. 7, 2005, and U.S. Patent Application Publication No. 2005/0113657, each of which is incorporated herein by reference in its entirety. The presently disclosed biosensors can be used or adapted for use in strips, implants, micro- and nano-particles, and the like.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs. While the following terms in relation to the methods of the presently disclosed subject matter are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

Following long-standing patent law convention, the terms "a," "an," and "the" refer to "one or more" when used in this application, including the claims. Thus, for example, reference to "a molecule" includes a plurality of molecules, unless the context clearly is to the contrary (e.g., a plurality of molecules), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Substrate Molding

Representative results were obtained with a polycarbonate (LEXAN®, HF 1110, SABIC Innovative Plastics, Pittsfield, Mass.) substrate, which offered high flow and low density. The polymer was dried at 250° F. for 4 hours before use. The raw polymer was mixed 0.2% by weight with t-butyl phenyl peroxide (Aldrich). Lauroyl peroxide (Aldrich Product #290785) and dicumyl peroxide (Fluka Product #36590) also are suitable for use with the presently disclosed methods. Benzoyl peroxide (Fluka Product #33581), however, did not produce satisfactory results.

The weight percent of peroxide could range from about 0.1% to about 0.4%. The polymer was allowed to cool before mixing, because the peroxide could react with the hot polymer. Once mixed, the polymer was fed to the molding machine, purged, and parts were molded as rapidly as possible. Cycle times longer than one minute produced defective parts. The molding machine (Ferromatik Milacron K100, Braunform GmbH, Bahlingen, Germany) conditions for a polycarbonate substrate are provided in Table 1. The best parts were 1.5 mm or less in thickness as determined by minimum autofluorescence.

TABLE 1

| Molding Machine Conditions for Polycarbonate Substrate | | | | | | | | |
|---|---|---|---|---|---|---|---|---|
| Barrel Nozzle | Barrel Front | Barrel 1 | Barrel 2 | Barrel Rear | Mold Temp | Injection Press | Injection Speed | Back Press |
| 520° F. | 560° F. | 560° F. | 540° F. | 480° F. | 210° F. | 2400 bar | 400 mm/sec | 80 psi |

A polystyrene (e.g., BASF, PS145D) substrate also can provide binding to the matrix (see FIG. 2) when treated by the presently disclosed methods. The molding machine conditions for a polycarbonate substrate are provided in Table 2.

TABLE 2

Molding Machine Conditions for Polystyene Substrate

| Barrel Nozzle | Barrel Front | Barrel 1 | Barrel 2 | Barrel Rear | Mold Temp | Injection Press | Injection Speed | Back Press |
|---|---|---|---|---|---|---|---|---|
| 440° F. | 490° F. | 490° F. | 440° F. | 380° F. | 170° F. | 2400 bar | 400 mm/sec | 80 psi |

Other polymers suitable for use with the presently disclosed methods include, but are not limited to the copolyester polyethylene terephthalate (PET) (DuraStar™ DS1010, Eastman Chemical Co., Kingsport, Tenn.) and polypropylene (PH592, LyondellBasell, Rotterdam, Netherlands)

Example 2

Matrix Preparation

Materials.

The following materials were used as received unless indicated otherwise: polyethylene glycol 1000 dimethacrylate (PEGDMA 1000) (Degussa Product #6874-0); 2-hydroxy-2-methylpropiophenone photoinitiator (PI) (Aldrich Product #405655); 6-arm polyethylene glycol (PEG) with acrylate terminations, molecular weight (MW) 10,000/arm (Biolink Product #BLS-018-083); Sorbitol (Aldrich Product #S1876); phosphate buffer (PBS); glucose binding protein (GBP) GBP=3MNBD solution (1 mg/mL) (Paragon Bioservices, Baltimore, Md.); and UV light, 200-500 Watts Hg Arc lamp (Oriel Instruments, Stratford, Conn.).

Other photoinitiators suitable for use with the presently disclosed methods include 2-2-Dimethyl-2 phenyl acetophenone (Aldrich Product #A6118); p-(octyloxyphenyl)phenyliodonium hexafluoroantimonate, Gelest, Inc., Morrisville Pa.); bis-acyl-phosphine oxide (BAPO) in water (Irgacure® 819DW, Ciba (BASF)); and a liquid mixture of an oligomeric α-hydroxyketone (oligomeric 2-hydroxy-2-methyl-1, 4-(1-methylvinyl)-phenylpropanone) and 2-hydroxy-2-methyl-1-phenyl-1-propanone (SarCure™ SR1129, Sartomer USA, LLC, Exton, Pa.). Neither a blend of 2,4,6-trimethylbenzoyldiphenyl phosphine oxide, 2,4,6-trimethylbenzophenone, 4-methylbenzophenone and oligo (2-hydroxy-2-methyl-1-(4-(-methylvinyl)phenyl)propanone) (SarCure™ SR1135 (Sartomer)) nor anthraquinone 2 sulfonic Na salt monohydrate (Aldrich) produced satisfactory results.

Preparation of Hydrogel Containing Protein-Reporter Group.

In a glass container, 200 μL of PEGDMA1000 MW, 2.5 μL of 6-arm PEG with acrylate terminations, 1 μL of photo initiator, and 8.25 mg of sorbitol were mixed with 450 μL of PBS. The mixture was vortexed for 15 seconds and then 150 μL of GBP-3MNBD protein-reporter group (2 mg/dL) were added.

Once the matrix was prepared, it was dispensed (1.2 μL) into each well of the molded polycarbonate plates and then UV-cured for 2 min. After curing, the plate-matrix device can be tested wet. Alternatively, the wet matrix was dispensed into each well of the molded polycarbonate plates, as above, and then placed in an oven under vacuum for 15 min to dry the matrix (see FIG. 1). The matrix stayed in place and several analytical tests could be performed on the plate-matrix device. Representative results using polystyrene as the substrate in the dry process are provided in FIG. 2.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

U.S. Patent Publication No. 2005/0255327 for Articles Having Bioactive Surfaces and Solvent-Free Methods of Preparation Thereof to Channey et al.;

U.S. Patent Application Publication No. 2005/0113658 for Fiber Optic Device for Sensing Analytes and Method of Making Same to Jacobson et al.;

U.S. Patent Application Publication No. 2011/0184168, for Long Wavelength Thiol-Reactive Fluorophores, to J. B. Pitner, et al., published Jul. 28, 2011;

U.S. Patent Application Publication No. 2011/0054390, for Extended Use Medical Device, to G. Searle, et al., published Mar. 3, 2011;

U.S. Patent Application Publication No. 2010/0167417, for Long Wavelength Thiol-Reactive Fluorophores, to J. B. Pitner, et al., published Jul. 1, 2010;

U.S. Patent Application Publication No. 2010/0003763, for Long Wavelength Thiol-Reactive Fluorophores, to J. B. Pitner, et al., published Jan. 7, 2010;

U.S. Patent Application Publication No. 2009/0124997, for Methods and Devices for Improving Delivery of a Substance to Skin, to R. J. Pettis, et al., published May 14, 2009;

U.S. Patent Application Publication No. 2009/0104714, for Visual Glucose Sensor and Methods of Use Thereof, to J. Thomas, et al., published Apr. 23, 2009;

U.S. Patent Application Publication No. 2008/0311675, for Dyes Having Ratiometric Fluorescence Response for Detecting Metabolites, to J. Thomas, et al., published Dec. 18, 2008;

U.S. Patent Application Publication No. 2006/0280652, for Long Wavelength Thiol-Reactive Fluorophores, to J. B. Pitner, et al., published Dec. 14, 2006;

U.S. Patent Application Publication No. 2005/0163711, for Intra-Dermal Delivery of Biologically Active Agents, to C. M. Nycz, et al., published Jul. 28, 2005;

U.S. Patent Application Publication No. 2005/0113658, for Fiber Optic Device for Sensing Analytes and Method of Making Same, to R. W. Jacobson, et al., published May 26, 2005;

U.S. Pat. No. 8,129,525, for Long Wavelength Thiol-Reactive Fluorophores, to J. B. Pitner, et al., issued Mar. 6, 2012;

U.S. Pat. No. 8,071,794, for Long Wavelength Thiol-Reactive Fluorophores, to J. B. Pitner, et al., issued Dec. 6, 2011;

U.S. Pat. No. 7,951,605, for Multianalyte Sensor, to J. B. Pitner, et al., issued May 31, 2011;

U.S. Pat. No. 7,851,593, for Binding Proteins as Biosensors, to H. V. Hsieh, et al., issued Dec. 14, 2010;

U.S. Pat. No. 7,815,922, for Articles Having Bioactive Surfaces and Solvent-Free Methods of Preparation Thereof, to B. Chaney, et al., issued Oct. 19, 2010;

U.S. Pat. No. 7,792,561, for Fiber Optic Device for Sensing Analytes, to J. Alarcon, et al., issued Sep. 7, 2010;

U.S. Pat. No. 7,787,923, for Fiber Optic Device for Sensing Analytes and Method of Making Same, to J. Alarcon, et al., issued Aug. 31, 2010;

U.S. Pat. No. 7,767,821, for Long Wavelength Thiol-Reactive Fluorophores, to J. B. Pitner, et al., issued Aug. 3, 2010;

U.S. Pat. No. 7,687,263, for In Vitro Tumor Angiogenesis Model, to M. Wu, et al., issued Mar. 30, 2010;

U.S. Pat. No. 7,629,172, for Entrapped Binding Protein as Biosensors, J to. Alarcon, et al., issued Dec. 8, 2009;

U.S. Pat. No. 7,563,891, for Long Wavelength Thiol-Reactive Fluorophores, to J. B. Pitner, et al., issued Jul. 21, 2009;

U.S. Pat. No. 7,496,392, for Fiber Optic Device for Sensing Analytes, to J. Alarcon, et al., issued Feb. 24, 2009;

U.S. Pat. No. 7,326,538, for Binding Proteins as Biosensors, to J. B. Pitner, et al., issued Feb. 5, 2008;

U.S. Pat. No. 7,316,909, for Binding Protein as Biosensors, to J. B. Pitner, et al., issued Jan. 8, 2008;

U.S. Pat. No. 7,064,103, for Binding Protein as Biosensors, to J. B. Pitner, et al., issued Jun. 20, 2006;

U.S. Pat. No. 6,855,556, for Binding Protein as Biosensors, to T. J. Amiss, et al., issued Feb. 15, 2005;

U.S. Pat. No. 6,576,430, for Detection of Ligands by Refractive Surface Methods, to H. V. Hsieh, et al., issued Jun. 10, 2003;

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for adhering a hydrogel matrix to a molded polymer substrate, the method comprising: (a) molding a mixture of a polymer comprising one or more polymer chains and an oxidizer to form a molded polymer substrate, wherein the oxidizer breaks the one or more polymer chains, and wherein the one or more polymer chains can recombine while retaining one or more putative radicals in the molded polymer substrate; (b) providing a hydrogel matrix comprising a hydrogel, a component comprising one or more acrylate groups or another functional group that can form one or more radicals upon polymerization in the molded polymer substrate, and a photoinitiator; (c) combining the molded polymer substrate and the hydrogel matrix; and (d) curing the combined molded polymer substrate and hydrogel matrix for a period of time to covalently bind the hydrogel matrix to the molded polymer substrate, thereby adhering the hydrogel matrix to the molded polymer substrate.

2. The method of claim 1, wherein the hydrogel matrix comprises polyethylene glycol dimethacrylate.

3. The method of claim 1, wherein the component comprising one or more acrylate groups comprises a polyethylene glycol having one or more terminal acrylate groups.

4. The method of claim 1, wherein the polymer comprises a material selected from the group consisting of a polycarbonate, a polystyrene, a polyethylene, a copolyester, and a polypropylene.

5. The method of claim 1, wherein the oxidizer comprises a peroxide.

6. The method of claim 5, wherein the peroxide is selected from the group consisting of t-butyl phenyl peroxide, lauroyl peroxide, and dicumyl peroxide.

7. The method of claim 6, wherein the peroxide is t-butyl phenyl peroxide.

8. The method of claim 5, wherein the peroxide is mixed with the polymer at a weight percent ranging from about 0.1% to about 0.4%.

9. The method of claim 8, wherein the peroxide is mixed with the polymer at a weight percent of about 0.2%.

10. The method of claim 1, wherein the initiator is selected from the group consisting of 2-hydroxy-2-methylpropiophenone, 2,2-dimethyl-2-phenylacetophenone, p-(octyloxyphenyl)phenyliodonium hexafluoroantimonate, bis-acyl-phosphine oxide (BAPO) in water, and a liquid mixture of an oligomeric .alpha.-hydroxyketone (oligomeric 2-hydroxy-2-methyl-1,4-(1-methylvinyl)-phenylpropanone) and 2-hydroxy-2-methyl-1-phenyl-1-propanone.

11. The method of claim 10, wherein the initiator is 2-hydroxy-2-methylpropiophenone.

12. The method of claim 1, wherein the curing comprises a process selected from the group consisting of heat, ultraviolet (UV) light, or a combination thereof.

13. The method of claim 1, wherein the hydrogel matrix further comprises a protein-reporter group.

14. The method of claim 13, wherein the protein comprises a glucose binding protein (GBP).

15. The method of claim 13, wherein the reporter group comprise a fluorescent dye.

* * * * *